(12) United States Patent
Burkhardt et al.

(10) Patent No.: US 8,040,505 B2
(45) Date of Patent: Oct. 18, 2011

(54) DEVICE AND METHOD FOR SEPARATING A LIQUID COMPONENT OF A BLOOD SAMPLE, AND ANALYZER APPARATUS COMPRISING SUCH A DEVICE

(75) Inventors: Claudius Burkhardt, Lucerne (CH); Hans-Peter Wahl, Huenenberg (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/506,323

(22) Filed: Jul. 21, 2009

(65) Prior Publication Data
US 2010/0011887 A1    Jan. 21, 2010

Related U.S. Application Data

(63) Continuation of application No. PCT/EP2008/000575, filed on Jan. 25, 2008.

(30) Foreign Application Priority Data

Jan. 25, 2007 (EP) ...................... 07001572

(51) Int. Cl.
*G01N 1/10* (2006.01)
*G01N 21/00* (2006.01)
*B01L 3/00* (2006.01)
*B01D 61/00* (2006.01)

(52) U.S. Cl. .......... 356/246; 210/789; 210/650; 422/72; 73/863; 356/436

(58) Field of Classification Search .............. 356/39–41, 356/244, 246, 436; 494/4, 7, 10, 27, 40–42; 210/85, 86, 789, 650; 73/863.23
See application file for complete search history.

(56) References Cited

U.S. PATENT DOCUMENTS

| | | | |
|---|---|---|---|
| 3,982,691 A | 9/1976 | Schultz | |
| 4,197,287 A * | 4/1980 | Piasio et al. | 435/7.92 |
| 4,509,941 A * | 4/1985 | Johnson | 494/45 |
| 4,865,106 A * | 9/1989 | Wichelman | 160/84.04 |
| 4,954,264 A * | 9/1990 | Smith | 210/782 |
| 4,957,637 A * | 9/1990 | Cornell | 210/782 |
| 4,981,585 A | 1/1991 | Kelley et al. | |
| 5,275,731 A * | 1/1994 | Jahn | 210/518 |
| 5,308,506 A * | 5/1994 | McEwen et al. | 210/745 |
| 5,763,265 A * | 6/1998 | Itsuzaki et al. | 435/288.7 |
| 5,853,600 A * | 12/1998 | McNeal et al. | 210/789 |
| 5,935,051 A * | 8/1999 | Bell | 494/4 |
| 6,291,249 B1 * | 9/2001 | Mahant et al. | 436/177 |
| 6,302,836 B1 * | 10/2001 | North, Jr. | 494/37 |
| 7,731,898 B2 * | 6/2010 | Burkhardt et al. | 422/64 |

FOREIGN PATENT DOCUMENTS

EP    0 272 915 A2    12/1987

* cited by examiner

*Primary Examiner* — Sang Nguyen
(74) *Attorney, Agent, or Firm* — Dinsmore & Shohl LLP

(57) ABSTRACT

A device for separating at least part of the liquid component of a blood sample and methods thereof are disclosed. Generally, the device includes a container body for receiving the blood sample, a layer of retaining porous material, a layer of separating permeable material. The retaining porous material retains non-liquid components of the blood sample after the non-liquid components have been subjected to centrifugal force which forces them through the separating permeable material into the retaining porous material.

7 Claims, 9 Drawing Sheets

DEVICE AND METHOD FOR SEPARATING A LIQUID COMPONENT OF A BLOOD SAMPLE, AND ANALYZER APPARATUS COMPRISING SUCH A DEVICE

CROSS REFERENCE TO RELATED APPLICATIONS

This application is a continuation of International Application No. PCT/EP2008/000575 filed Jan. 25, 2008, which claims priority to EP Application No. 07001572.2, filed Jan. 25, 2007.

TECHNICAL FIELD

Embodiments of the invention concerns a device and a method for separating at least part of a liquid component of a blood sample, and an analyzer apparatus comprising a device of the above mentioned kind.

BACKGROUND

The separation of liquid components of blood samples, e.g. plasma and serum, is a necessary and important pre-analytical step in clinical diagnostics.

Known methods for performing the above mentioned separation require a considerable amount of manual work and time. The automation of that manual work, both in terms of throughput, workflow and reliability, becomes essential.

An important parameter is the time required for plasma or serum separation during centrifugation. This time could be substantially reduced by centrifugation of the sample tube around its axis of symmetry instead of using the conventional swing bucket method. This is because the length of the motion path followed by cell components of blood sample during centrifugation of the sample container about its symmetry axis is much shorter than in a conventional swing bucket centrifugation of a primary sample tube. When swing bucket centrifugation of a sample tube containing a blood sample is performed the rotation axis is perpendicular to the length axis of the sample tube and the motion path followed by cell components of blood sample during the centrifugation is much longer because the cell components move along the length axis of the sample tube towards the bottom of this tube.

If a primary sample tube is used for example as a sample container for centrifugation around its axis of symmetry, the length of the motion path followed by cell components of blood sample during centrifugation is less than the length of the radius of the primary sample tube, e.g. between 1 and 4 mm.

A problem associated with primary sample tube centrifugation around its axis of symmetry is the maintenance of the separation after centrifugation is stopped. The separated non liquid components are only temporary stuck against the internal wall of the sample tube and will mix again with the liquid component to then slowly sediment at the bottom of the tube.

In U.S. Pat. No. 4,509,941 a sample tube is disclosed comprising a porous material for entrapping blood cells when the tube is centrifuged along its vertical axis. A particularly designed cap helps to keep the porous material in place against the interior wall of the tube. A problem however remains, as the blood cells are not steadily trapped in the porous material. The same document discloses that plasma itself can be used to release the red blood cells from said material. This means that if the separated plasma is not removed quickly, it will be contaminated again by the blood cells.

SUMMARY

Embodiments of the present invention provide a device for separating at least part of the liquid component of a blood sample and prevent the non-liquid components of the blood sample from returning into the separated part of liquid component. This is achieved by means of a layer of a suitable separating permeable material, acting as a barrier for the passive leaking of blood cells from a retaining porous material, while allowing blood cells to pass through when subjected to centrifugal force.

Embodiments of the present invention also increase the processing throughput and provide more than one volume of plasma by providing a device for simultaneously separating at least part of the liquid components of different blood samples. This is achieved by dividing the inventive device into a plurality of sections and respective sample compartments, separated by partition walls.

Another advantage of the embodiments of the present invention is the enablement of tests like quality checks already in the separation device. This is achieved by integrating a photometric chamber for collecting part of the separated liquid component at the bottom of the inventive device.

In one embodiment, a separation device for separating at least part of the liquid component of a blood sample is disclosed. The separation device comprises a container body, at least one sample compartment for receiving the blood sample and retaining at least part of the separated liquid component after separation, at least one layer of a retaining porous material, and at least one layer of a separating permeable material. The retaining porous material retains non-liquid components of the blood sample, after the non-liquid components have been subjected to centrifugal force which forces them through the layer of separating permeable material into the retaining porous material.

In another embodiment, a separation device for separating at least part of the liquid component of a blood sample is disclosed. The device comprises a container body, at least one sample compartment for receiving the blood sample and retaining at least part of the separated liquid component after separation, at least one layer of retaining porous material for retaining non-liquid components of the blood sample, and at least one photometric chamber, which is fluidically connected with at least one sample compartment. The photometric chamber collects at least a part of the separated liquid component and is configured and dimensioned for enabling photometric measurement of the liquid component therein collected.

In still another embodiment, a separation device for separating at least part of the liquid component of at least one blood sample is disclosed. The device comprises a container body being divided into a plurality of sections by partition walls, and a plurality of sample compartments for receiving a plurality of the blood samples and retaining at least part of the separated liquid component after separation, wherein at least one of the sections comprises a layer of retaining porous material for retaining non-liquid components of the blood sample after separation.

The subject invention will now be described in terms of its preferred embodiments with reference to the accompanying drawings. These embodiments are set forth to aid the understanding of the invention, but are not to be construed as limiting.

BRIEF DESCRIPTION OF THE DRAWINGS

FIG. 3 schematically shows the separation of the blood sample into its non-liquid components 32 and its liquid component 33.

FIG. 5 shows in more detail the spatial distribution of the non-liquid components 32 and the liquid component 33 of a blood sample at the end of the centrifugation of the container body 11 about its symmetry axis 13.

FIG. 8 schematically shows the separation of the blood sample into its non-liquid components 32 and its liquid component 33.

FIG. 16 shows photometric chambers 102 and 106 which are fluidically connected with compartments 52 and 56 respectively and which are suitable for performing photometric measurements.

FIG. 17 shows only one of the compartments of this variant and shows a photometric chamber 132 which is fluidically connected with a compartment 52 and which is suitable for performing photometric measurements.

Figure 1:
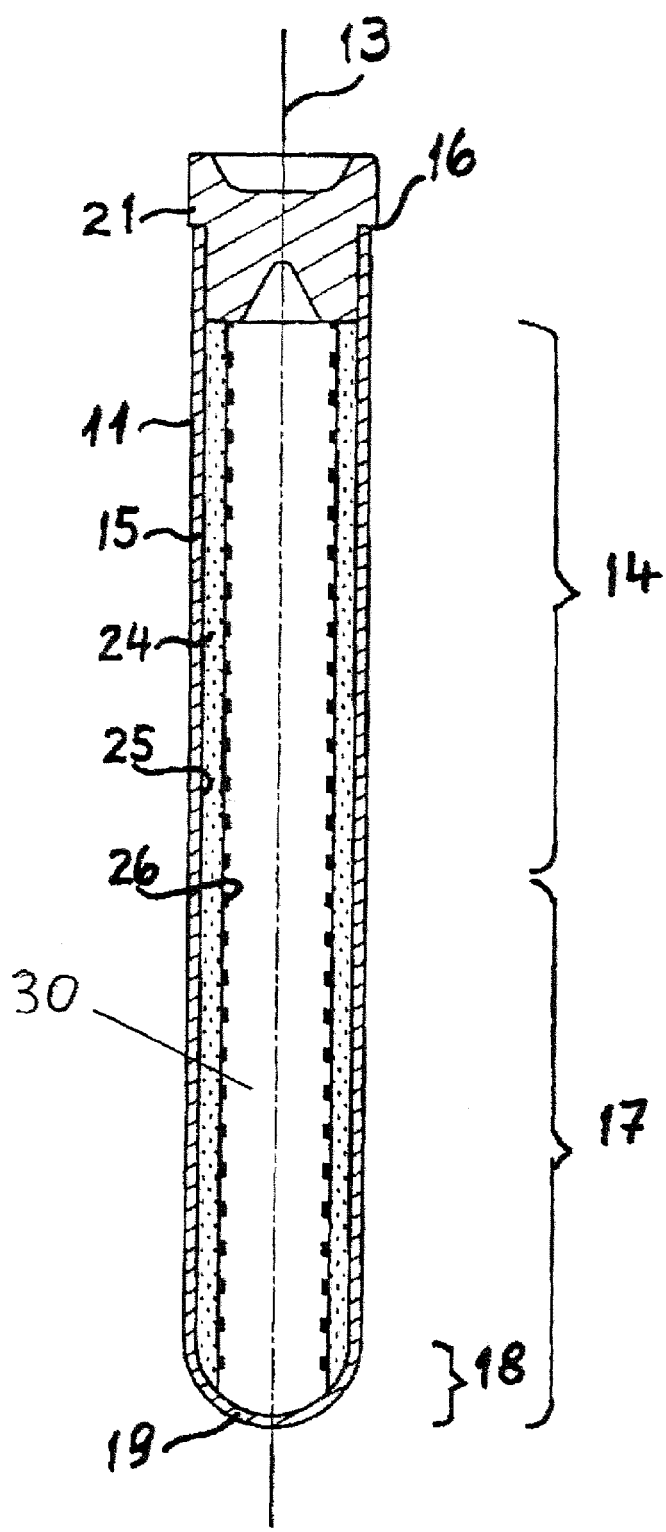
FIG. 1 is a cross-sectional view of a first embodiment of a device according to the invention, the cross-section being taken along a plane passing through the symmetry axis 13 of a container body 11.
Figure 2:
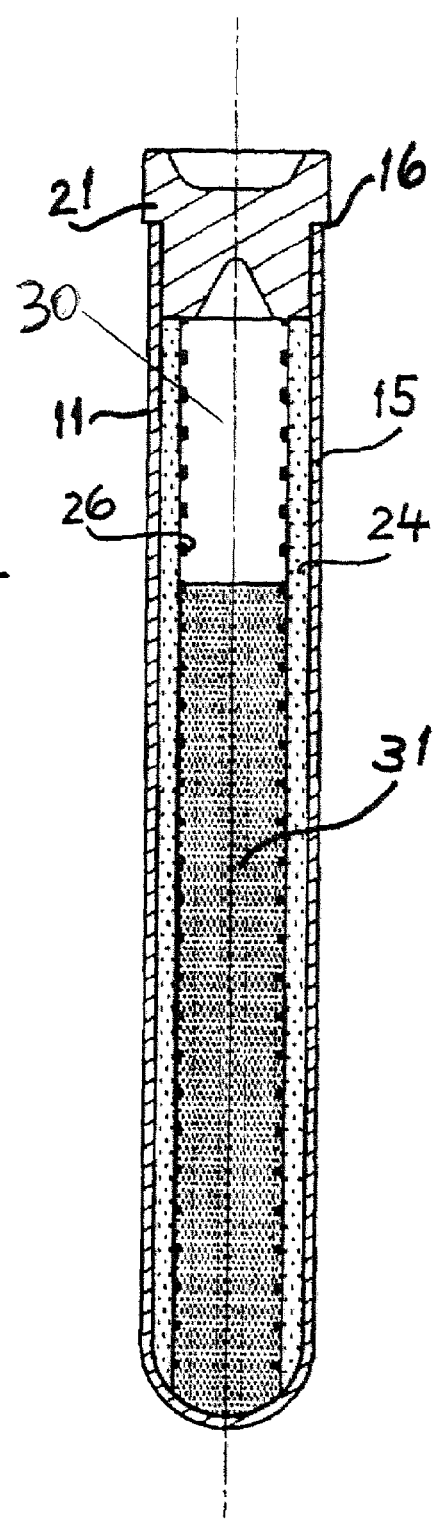
FIG. 2 is a cross-sectional view of the container body 11 like the one shown by FIG. 1 and of a blood sample 31 contained in container body 11.

REFERENCE NUMERALS USED IN DRAWINGS 11 single compartment container body or sample tube
13 axis of rotation for axial centrifugation of container body 11
14 upper portion of container body 11
15 side wall of container body 11
16 upper opening of container body 11
17 lower portion of container body 11
18 bottom region of container body 11
19 bottom wall of container body 11
21 cap of container body 11
22 photometric chamber connected with the interior of container body 11
23 opening in the bottom wall 16 of container body 11
24 layer of retaining porous material
24a outer annular portion of layer 24
24b inner annular portion of layer 24
25 inner surface of cylindrical side wall 15
26 layer of permeable separating material
27 air
30 sample compartment of container body 11
31 blood sample
32 non-liquid components of blood sample 31
33 liquid component of blood sample 31
41 multi-compartment container body
43 axis of rotation for axial centrifugation of container body 41
44 upper portion of container body 41
45 side wall of container body
46 upper opening of container body 41
47 lower portion of container body 41
48 inclined side wall of container body 41
49 bottom wall of container body 41
50 arrow
51-58 sample compartment of container body 41
61-68 partition wall of container body 41
72 bottom region of compartment 52
76 bottom region of compartment 56
82 cover of upper opening 46 of container body 41
84 layer of retaining porous material
84a outer portion of layer 84
84b inner portion of layer 84
85 inner surface of side wall 45
86 layer of permeable separating material
87 air
88 pipetting opening/pierceable pipetting opening
89 pipetting opening/pierceable pipetting opening
92 opening in the bottom wall of compartment 52
96 opening in the bottom wall of compartment 56
102 photometric chamber connected with compartment 52
106 photometric chamber connected with compartment 56
112 mirror arranged within cup 102
116 mirror arranged within cup 106
121 incident light beam
122 reflected light beam
123 incident light beam
124 reflected light beam
130 arrow
132 photometric chamber connected with compartment 52
141 mirror
142 mirror
143 incident light beam
144 reflected light beam 145 reflected light beam
151—
158 section of container body 41
312 blood sample in compartment 52
316 blood sample in compartment 56
322 non-liquid component of blood sample 312
326 non-liquid component of blood sample 316
332 liquid component of blood sample 312
336 liquid component of blood sample 316

DETAILED DESCRIPTION

Embodiments of the present invention refers to a separation device for separating at least part of the liquid component of a blood sample, said separation device comprising a container body, at least one sample compartment for receiving said blood sample and retaining at least part of said separated liquid component after separation, a layer of retaining porous material, a layer of separating permeable material, wherein said retaining porous material is retaining non-liquid components of said blood sample, after said non-liquid components have been subjected to centrifugal force, forcing them through said separating permeable material into said retaining porous material.

For non-liquid components of blood is intended particulate matter with a density such that separation by gravity or centrifugation can be allowed within a relatively short time. Examples are blood cells, cell aggregates, micro-clots, etc. This may not comprise very small components eventually present such as viruses.

A liquid component of blood is in the first place plasma or serum and its components such as proteins, electrolytes, etc. after the non-liquid components have been separated.

According to the present invention a separating permeable material is a material comprising a large number of closely-spaced holes sized for the passage of matter with a size typical of non-liquid components of a blood sample under centrifugation conditions but preventing passage under steady conditions. The separating permeable material may have the shape of a mesh or stent and is preferably made of a an inert polymer, preferably hydrophobic, preferably having a contact angle comprised between 90 and 140 degrees. The size of said holes or mesh opening is preferably comprised between 90 and 200 micrometers. Inert means, not interacting with the blood sample. Suitable materials are for example Nylon, Teflon or the like. An example of suitable material is Nitex Nylon 03-171 manufactured by Sefar, Switzerland. The function of said material is therefore more than simply structural. More than keeping the layer of retaining porous material in place, such materials ensure a better down flow of the separated liquid component of the blood sample after centrifugation and prevents the non-liquid components of the blood sample from returning into the separated part of liquid component.

A retaining porous material is a material in which non-liquid components of a blood sample can be accumulated when subjected to centrifugal force in direction of said material, so that the non-liquid components can be retained inside the pores. This material is preferably chosen from a group comprising an open cell foam, a foamed rubber, a fleece, a mat, a honeycomb-like material or the like, and has a volume preferably larger than the volume of the non-liquid components to be retained. An example of suitable material is the foam S6050HY by KOEPP Schaum GmbH, Germany, available in reticulated and non reticulated form.

According to a preferred embodiment said container body is divided into a plurality of sections by partition walls. A layer of said retaining porous material and a layer of said separating porous material are arranged in at least one of said sections.

A separation device according to the present invention may therefore comprise a single sample compartment, for separating at least part of the liquid component of a blood sample or a plurality of compartments for the simultaneous separation of at least part of the liquid components of a plurality of blood samples.

Both kinds of devices have:
a vertical axis of rotation,
at least one sample compartment for receiving said blood sample and retaining at least part of said separated liquid component after separation, said at least one sample compartment being located between said axis of rotation and a layer of separating permeable material, and
a layer of retaining porous material located between said layer of separating permeable material and the side wall of the container body.

It is recognizable that the separation conditions and thus the separation efficiency in case of a multi-compartment device are similar to those of a single-compartment device where separation is carried out by centrifugation around the axis of symmetry.

Centrifuges required for rotating said separation devices, around said vertical axis of rotation, can be small and thus suitable for being integrated as an automatically operated centrifuge into a clinical diagnostic analyzer apparatus. Such analyzer apparatus may comprise one or a few of such centrifuges for all of the samples in the analyzer apparatus. Such centrifuge, however, can also be a stand-alone device or can be integrated into another device as e.g. a sample preparation unit.

As these separation devices comprise one or a few compartments, preferably an even number of compartments as e.g. 2, 4, 6, 8, 12, 18, they are also well suitable for the fast processing of small batches.

Liquid component separated in a device according to the invention is preferably taken out before analysis by means of a pipetting needle. The pipetting needle is preferably part of an automatic pipetting unit of an analyzer apparatus. For sampling separated liquid component the pipetting needle may pierce a cover, which may close the device. This process is thus much simpler, faster and more convenient than the conventional methods, which require a conventional swing bucket centrifuge outside of the analyzer.

According to a preferred embodiment of the present invention, the separation device further comprises at least one photometric chamber, which is fluidically connected with said at least one sample compartment, said chamber collecting at least a part of the separated liquid component and being configured and dimensioned for enabling photometric or reflectometric measurements of said liquid component therein collected.

According to another embodiment, the present invention provides a separation device for separating at least part of the liquid component of at least one blood sample, said device comprising a container body, at least one sample compartment for receiving said blood sample and retaining at least part of said separated liquid component after separation, a layer of retaining porous material for retaining non-liquid components of said blood sample, and at least one photometric chamber which is fluidically connected with said at least one sample compartment, said photometric chamber collecting at least a part of the separated liquid component and being configured and dimensioned for enabling photometric measurement of said liquid component therein collected.

These embodiments make thus possible to perform sample integrity checks including measurement of serum indices. In this way, required integrity checks of the blood sample can be carried out automatically in the same separation device and by the same analyzer apparatus before the usual analysis of plasma or serum samples is carried out.

According to another embodiment, the present invention provides a separation device for separating at least part of the liquid component of at least one blood sample, said device comprising a container body being divided into a plurality of sections by partition walls, a plurality of sample compartments for receiving a plurality of said blood samples and retaining at least part of said separated liquid component after separation, wherein at least one of said sections comprises a layer of retaining porous material, for retaining non-liquid components of said blood sample after separation.

According to another embodiment, at least one of said sections further comprises a layer of separating permeable material, for preventing the non-liquid components of the blood sample from returning into the separated part of liquid component.

According to another embodiment said separation device further comprises at least one photometric chamber being fluidically connected with said at least one sample compartment through an opening in the bottom wall of the lower portion of said container body, said photometric chamber collecting at least a part of the separated liquid component and being configured and dimensioned for enabling a photometric measurement of said liquid component therein collected.

The present invention also refers to a method for separating at least part of the liquid component of at least one blood sample, said method comprising:
(a) providing a separation device according to any of the favorite embodiments,
(b) introducing a blood sample into the at least one sample compartment of said separation device,
(c) rotating said device about an axis at a predetermined speed for separating the liquid component of the blood sample from the non-liquid components thereof, and
(d) stopping said rotation, thereby allowing the separated liquid component of said at least one blood sample to flow towards the central and lower part of said at least one sample compartment, whereas the non-liquid components of the blood sample and a portion of the liquid component of the blood sample are retained by the layer of retaining porous material.

For the device embodiments comprising a photometric chamber, the method above may further comprise the step of effecting a photometric measurement of at least part of the liquid component collected in at least one photometric chamber of said device.

A clinical diagnostic analyzer apparatus according to the present invention may therefore comprise a device according to any of the embodiments, means for centrifuging said device about an axis, a detector for performing photometric or reflectometric measurements of the contents of a photometric chamber of said device.

The centrifugation time necessary for achieving plasma or serum separation with a device according to the invention is shorter than the centrifugation time required in the case of a conventional swing bucket centrifugation of a primary sample tube, because the cell components of the blood sample have to migrate along a shorter distance. In the embodiments shown by FIGS. 1 to 9, wherein the sample container is a sample tube, the migration distance of the cell components of the blood sample is less than half the length of the radius of the cross-section of the sample container. In the embodiments shown by FIGS. 10 to 17, the migration distance of the cell components of the blood sample is only about half the distance of the thickness of the layer of blood which is spun to the outer wall of the sample container.

First Example of a Device According to the Invention

A first example of a device according to the invention is described hereinafter with reference to FIG. 1.

The container body of the device is a sample tube 11 and a layer 24 of a retaining porous material is arranged within sample tube 11.

Sample tube 11 has a symmetry axis 13, a cylindrical side wall 15, an upper opening 16, a bottom region 18, and a bottom wall 19. The upper opening 16 of sample tube 11 is closed by a stopper or cap 21 which is pierceable by a pipetting needle. The interior of sample tube 11 comprises an upper portion 14 and a lower portion 17. The container further has a sample compartment for receiving a blood sample and retaining the separated part of liquid component.

The outer surface of layer 24 is in contact with and covers at least partially the inner surface 25 of the cylindrical side wall 15. In a preferred embodiment porous material layer 24 covers the entire inner surface 25 of the cylindrical side wall 15.

Layer 24 of porous material is suitable for retaining non-liquid components 32 of the blood sample 31.

Layer 24 of porous material is made of e.g. an open cell foam, a foamed rubber, a fleece, a mat, a honeycomb-like material or the like.

In a preferred embodiment the device comprises in addition a layer 26 of separating permeable material such as a mesh or stent, which is in contact with and extends at least partially over the inner surface of layer 24 of retaining porous material. In a preferred embodiment, layer 26 extends over the entire inner surface of layer 24.

The separating permeable material layer 26 is made preferably of a plastic material, e.g. Nylon, Teflon or the like. Layer 26 keeps layer 24 in place, ensures a better down flow of the separated part of liquid component of the blood sample and prevents the separated non-liquid components from returning into the separated part of liquid component.

First Example of a Method According to the Invention

Figure 3:
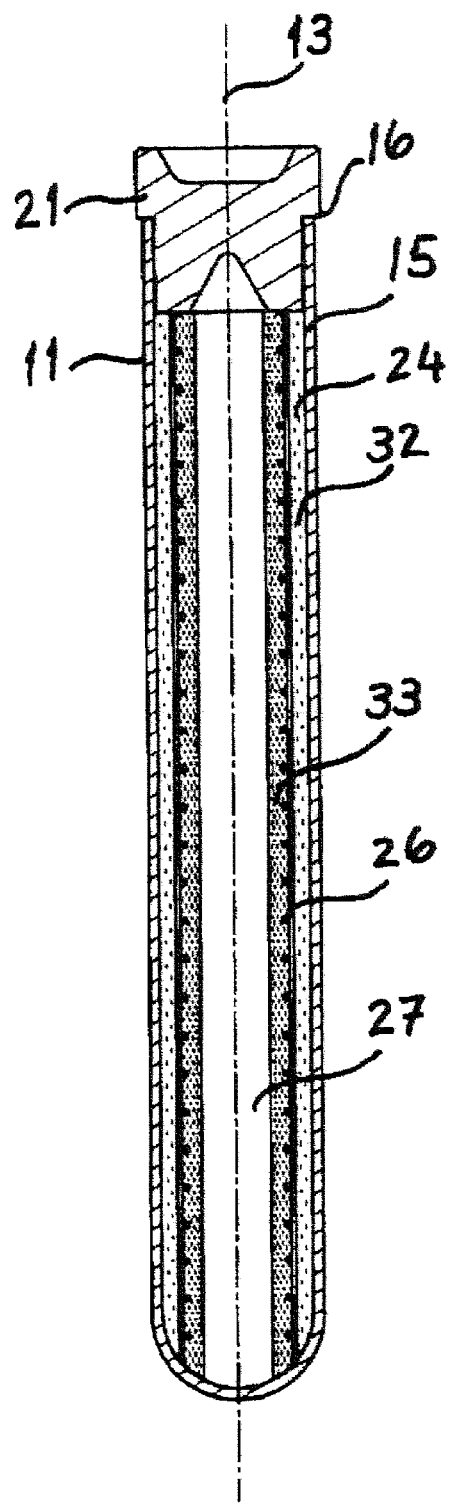
FIG. 3 is a cross-sectional view of the container body 11 like the one shown by FIG. 1 at the end of the axial centrifugation of the container body 11, the centrifugation being effected by spinning container body 11 about its symmetry axis 13.
Figure 4:
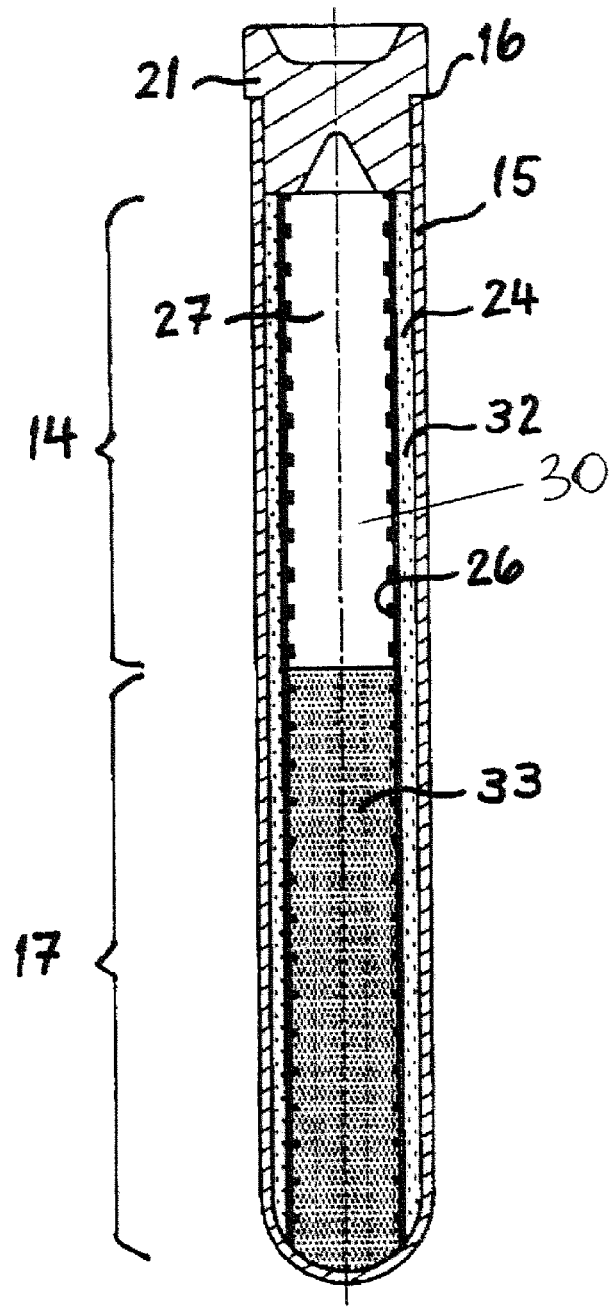
FIG. 4 is a cross-sectional view of the container body 11 like the one shown by FIG. 1 after centrifugation of the container body 11 about its symmetry axis and with this tube at rest.
Figure 5:
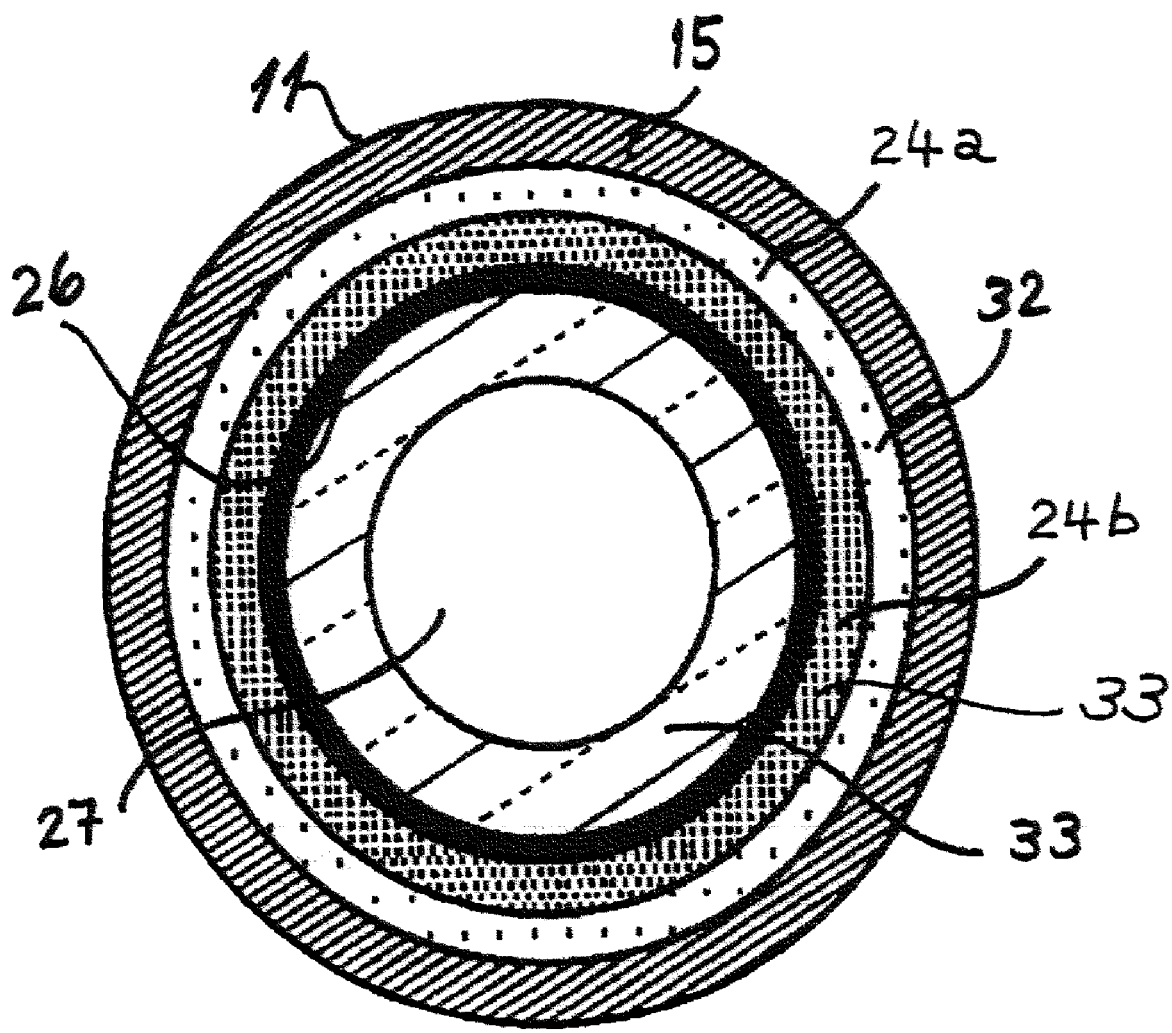
FIG. 5 is a cross-sectional, enlarged view of container body 11 shown by FIG. 3, the cross-sectional view being taken along a plane perpendicular to the symmetry axis of container body 11.

A first example of a method according to the invention for separating a liquid component from a blood sample makes use of the device described above with reference to FIG. 1 and comprises the following steps illustrated by FIGS. 2 to 5:
(a) introducing a blood sample 31 (shown in FIG. 2) into the sample compartment 30 of sample tube 11,
(b) rotating sample tube 11 about its symmetry axis 13 (as shown by FIGS. 3 and 5) at a predetermined speed for separating the liquid component of the blood sample from the non-liquid components thereof, and
(c) stopping the rotating of sample tube 11, thereby allowing the liquid component of the blood sample to flow towards the central and lower part of the sample compartment 30, whereas the non-liquid components of the blood sample 31 and a portion of the liquid component of the blood sample are retained by layer 24 of the retaining porous material.

Step (b) is carried out with a rotation speed adjusted to a value in a range between 1000 and 20000 rpm. The time required for the separation depends from the rotation speed. A decrease of the time required for the separation is obtained by increasing the rotation speed. In the case of centrifugation of the sample tube 11, the following are examples of rotation speeds used and of the values of the separation time achieved:

| | Rotation speed | |
|---|---|---|
| | 1000 rpm | 20000 rpm; |
| Separation time | 20 minutes | 15 seconds. |

With a rotation speed of 20000 rpm, separation of platelet-free plasma (<1000 platelets per μL) of a blood sample is achieved in a separation time lying in a range from 30 to 60 seconds.

After step (c) a portion of the liquid component of the blood sample can be collected by pipetting through the cap 21 while the non-liquid components of the blood sample 31 and a portion of the liquid component of the blood sample are retained by layer 24 of the retaining porous material.

Layer 26 of separating permeable material is located between the sample compartment 30 and the layer 24 of retaining porous material. Non-liquid components 32 of blood sample 31 can pass through layer 26 of separating permeable material during centrifugation, while layer 26 of separating permeable material prevents the non-liquid components 32 from returning into the separated part of liquid component in the sample compartment 30 after separation is completed.

The cross-sectional view shown by FIG. 5 shows the spatial distribution of the liquid component 33 and the non-liquid components 32 of blood sample 31 at the end of the axial centrifugation of sample tube 11 according to step (b) but before stopping the rotation of the above described method and as schematically represented by FIG. 3. As shown by FIG. 5, the non-liquid components 32 occupy an outer annular portion 24a of layer 24 of retaining porous material, whereas a first portion of the liquid component 33 occupies an inner annular portion 24b of layer 24 of retaining porous material and a second portion of the liquid component 33 occupies an annular space between layer 26 of separating permeable material and a space 27 occupied by air in the sample compartment 30.

In one embodiment of the above described method, sample tube 11 is a blood collection tube, the inside of which is under vacuum. This tube contains a coagulation preventing agent, and the blood sample 31 is introduced into the blood collection tube by venipuncture. In this case the liquid component 33 separated by the above described method is blood plasma.

In another embodiment of the above described method, sample tube 11 is a blood collection tube, the inside of which is under vacuum. This tube contains no coagulation preventing agent or contains a coagulation promoting agent, and the blood sample 31 is introduced into the blood collection tube by venipuncture. In this case the liquid component 33 separated by the above described method is blood serum.

After step (c) sample tube 11 and the separated liquid component 33 contained therein are usually kept at a suitable temperature until sample tube 11 and its contents are transferred to a clinical diagnostic analyzer apparatus for analysis of the liquid component 33. However, the entire process may be executed by the same clinical diagnostic analyzer apparatus. The liquid component 33 of the blood sample is then pipetted from sample tube 11 by means of a pipetting needle which pierces cap 21, enters sample tube 11 and aspirates the liquid component 33, which is transferred e.g. to a reaction cuvette of the clinical diagnostic analyzer apparatus.

Second Example of a Device According to the Invention

Figure 6:
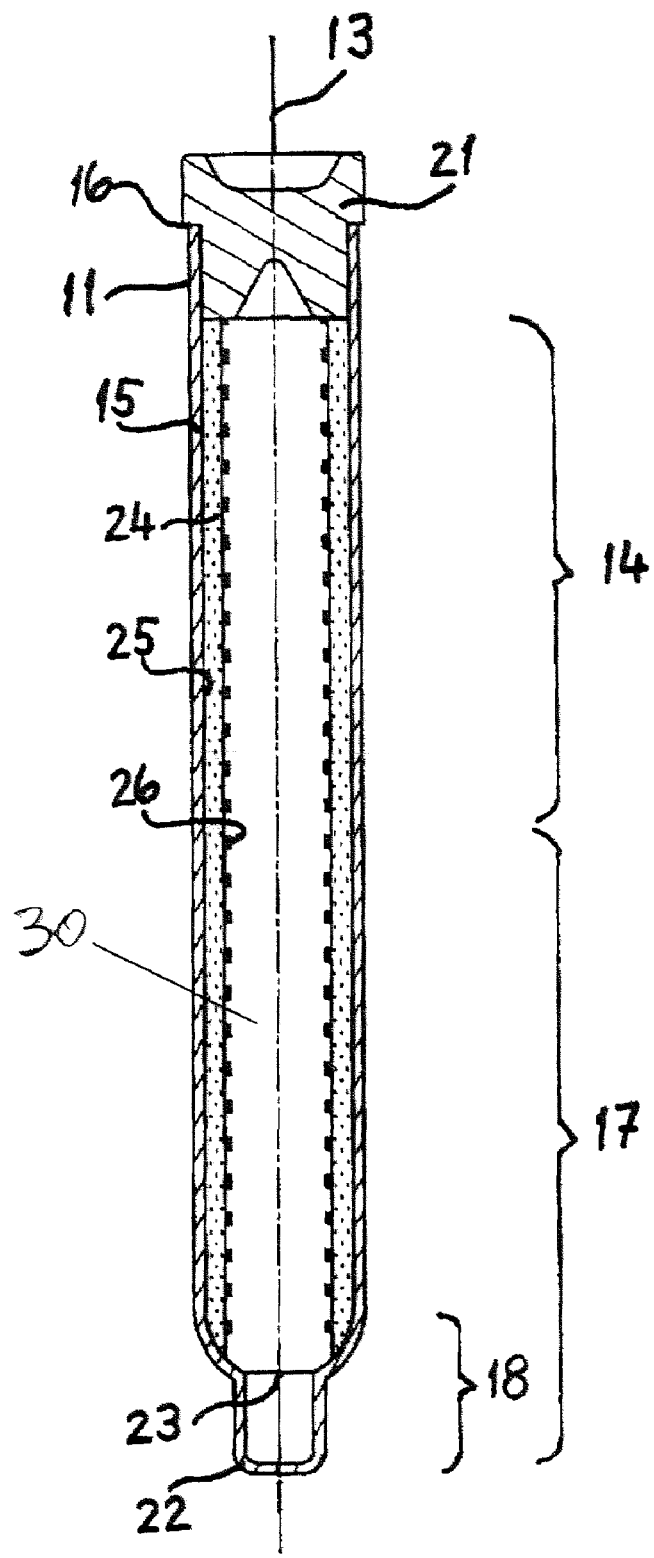
FIG. 6 is a cross-sectional view of a variant of the embodiment shown by FIG. 1 which comprises a photometric chamber 22 which is fluidically connected with the interior of container body 11 through an opening 23 in the bottom wall 19 and which is suitable for performing photometric measurements.

A second example of a device according to the invention is described hereinafter with reference to FIG. 6.

The structure of this second example is a variant of the structure of the example shown by FIG. 1. In this variant, sample tube 11 shown by FIG. 6 comprises in addition a photometric chamber 22, which is fluidically connected with sample compartment 30 through an opening 23 in the bottom wall 19 of sample tube 11. Photometric chamber 22 is configured and dimensioned for enabling photometric measurement of a liquid contained therein.

Second Example of a Method According to the Invention

Figure 7:
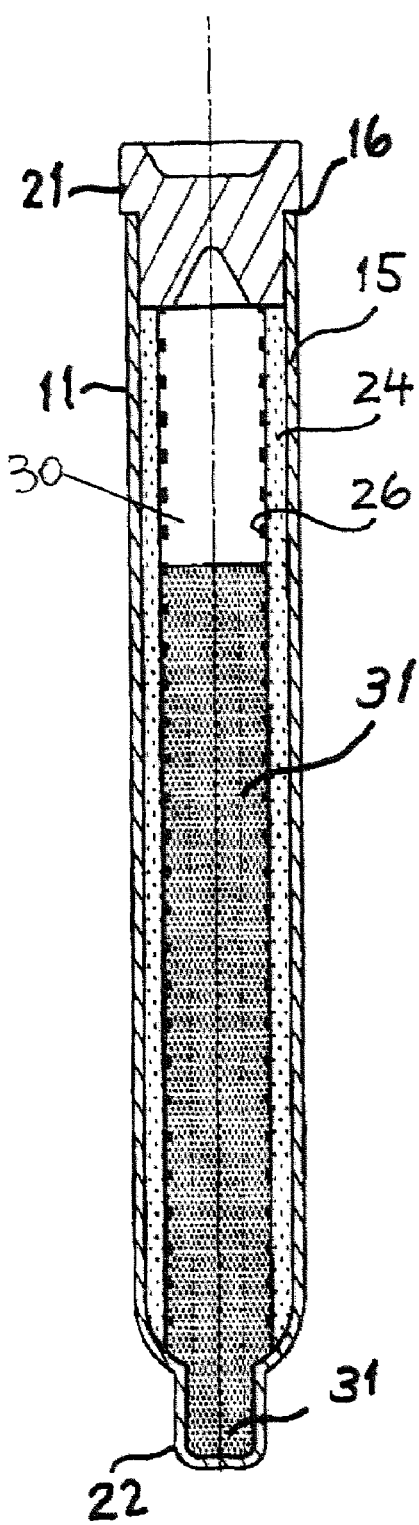
FIG. 7 is a cross-sectional view of the container body 11 like the one shown by FIG. 6 and of a blood sample 31 contained in container body 11.
Figure 8:
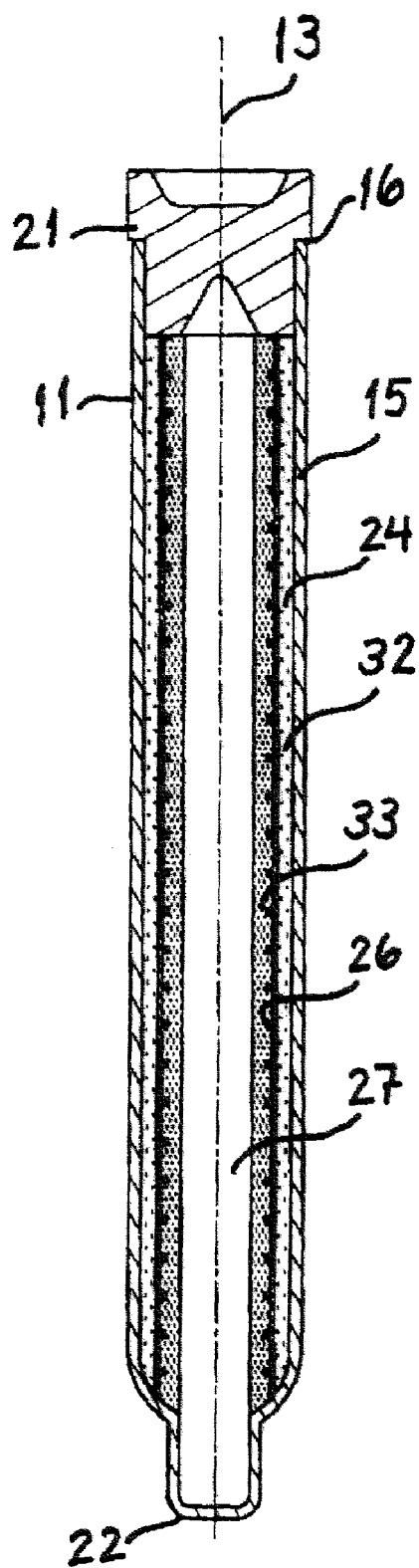
FIG. 8 is a cross-sectional view of the container body 11 like the one shown by FIG. 6 at the end of the axial centrifugation of the container body 11.
Figure 9:
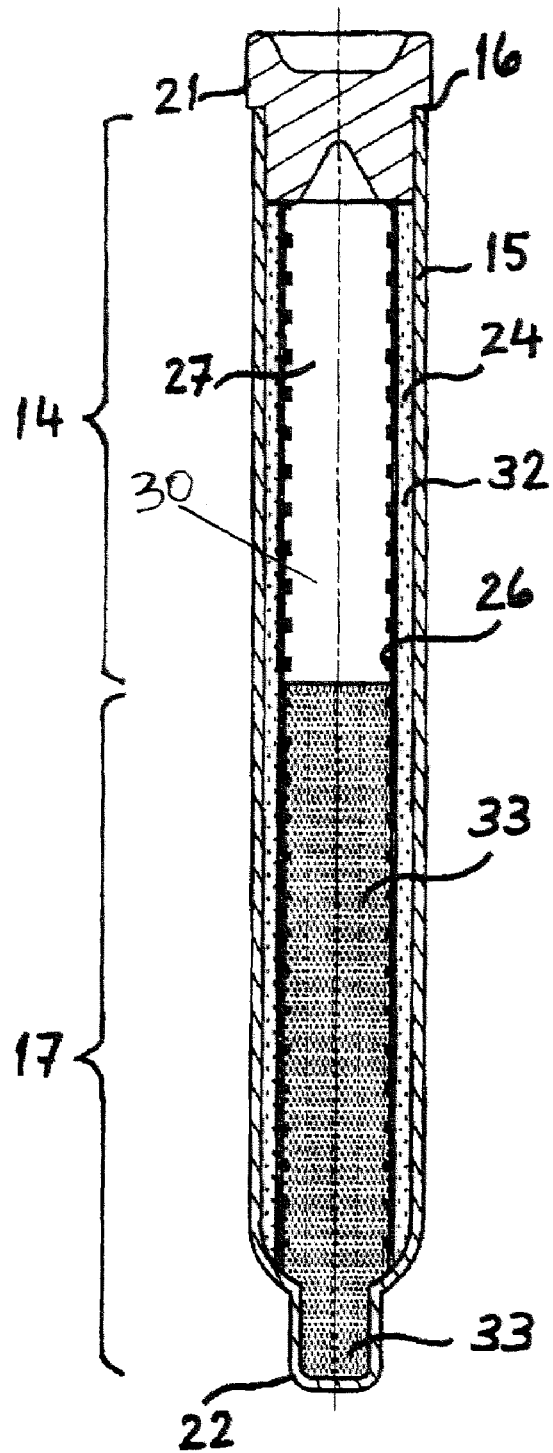
FIG. 9 is a cross-sectional view of the container body 11 like the one shown by FIG. 6 after axial centrifugation of the container body 11 and with this tube at rest.

A second example of a method according to the invention for separating a liquid component from a blood sample makes use of the device described above with reference to FIG. 6 and comprises the following steps illustrated by FIGS. 7 to 9:

(a) introducing a blood sample 31 (shown in FIG. 7) into sample compartment 30 of sample tube 11 (shown in FIG. 6), (b) rotating sample tube 11 about its symmetry axis 13 at a predetermined speed for separating the liquid component of the blood sample 31 from the non-liquid components thereof (as shown by FIG. 8), and (c) stopping the rotating of sample tube 11, thereby allowing the liquid component of the blood sample to flow towards the central and lower part of the sample compartment 30 and into photometric chamber 22, whereas the non-liquid components 32 of the blood sample 31 and a portion of the liquid component 33 of the blood sample are retained by layer 24 of the retaining porous material.

Step (b) is carried out as in the first example.

After step (c) a portion of the separated liquid component of the blood sample can be collected by pipetting through the cap 21 while the non-liquid components of the blood sample 31 and a portion of the liquid component of the blood sample are retained by layer 24 of the porous material.

In this second example of a method according to the invention a portion of separated liquid component 33 is collected in photometric chamber 22 and is therein photometrically evaluated.

In one embodiment of the above described method, sample tube 11 is a blood collection tube, the inside of which is under vacuum. This tube contains a coagulation preventing agent, and the blood sample 31 is introduced into the blood collection tube by venipuncture. In this case the portion of the liquid component 33 separated by the above described method and contained in photometric chamber 22 is blood plasma.

In another embodiment of the above described method, sample tube 11 is a blood collection tube, the inside of which is under vacuum. This tube contains no coagulation preventing agent or contains a coagulation promoting agent, and the blood sample 31 is introduced into the blood collection tube by venipuncture. In this case the portion of the liquid component 33 separated by the above described method and contained in photometric chamber 22 is blood serum.

In this case, sample integrity checks including measurement of serum indices can be performed by photometric measurement of the serum sample contained in photometric chamber 22.

The further processing of sample tube 11 after step (c) is e.g. as described above in the first example of a method according to the invention.

Third Example of a Device According to the Invention

A third example of a device according to the invention is described hereinafter with reference to FIGS. 10 to 12.

These figures refer to a multi-compartment device comprising a container body 41 which has a symmetry axis of rotation 43. As shown by FIG. 12, the interior of container body 41 is divided into a plurality of sections 51-58 and respective sample compartments 151-158 by partition walls 61-68. Each of compartments 51 to 58 is adapted for receiving a blood sample. All compartments 51 to 58 have preferably the same shape and the same size, and the number of compartments is preferably an even number. In a preferred embodiment the container is divided into 12 compartments. Each one of the sections 151 to 158 has a bottom region like 72 and 76 shown in FIG. 11. In a preferred embodiment container body 41 is a one-piece container body.

Container body 41 has an upper portion 44 and a lower portion 47. The upper portion 44 of container body 41 has a cylindrical side wall 45 and an upper opening 46. The lower portion 47 of container body 41 has the shape of a truncated cone and has a conical side wall 48 and a bottom wall 49.

Figure 10:
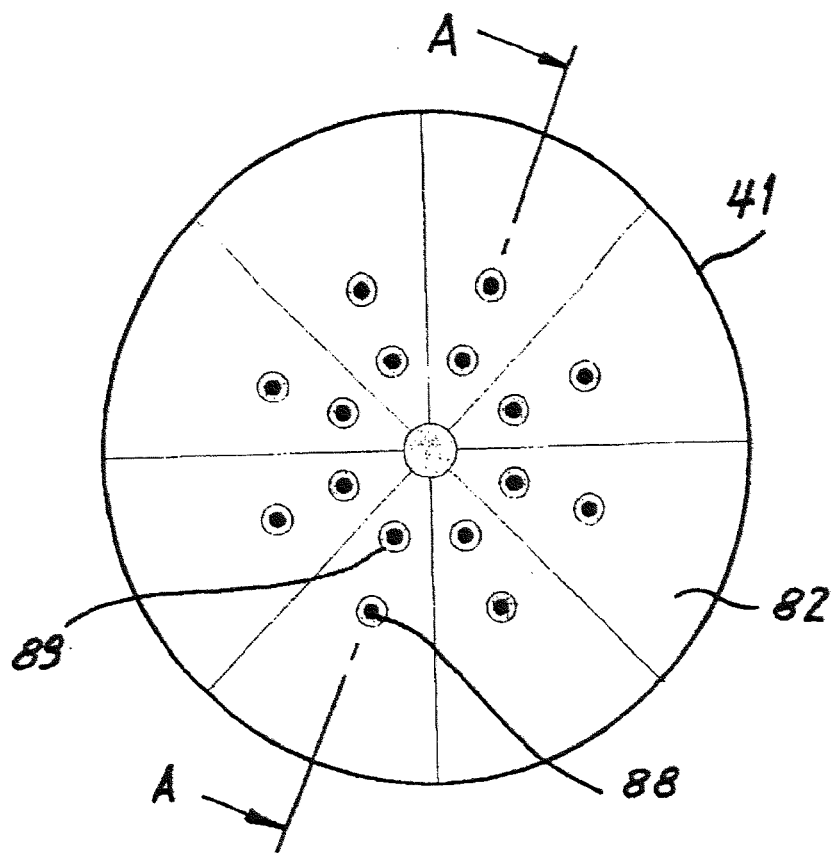
FIG. 10 shows a top plan view of a multi-compartment embodiment of a device according to the invention.
Figure 11:
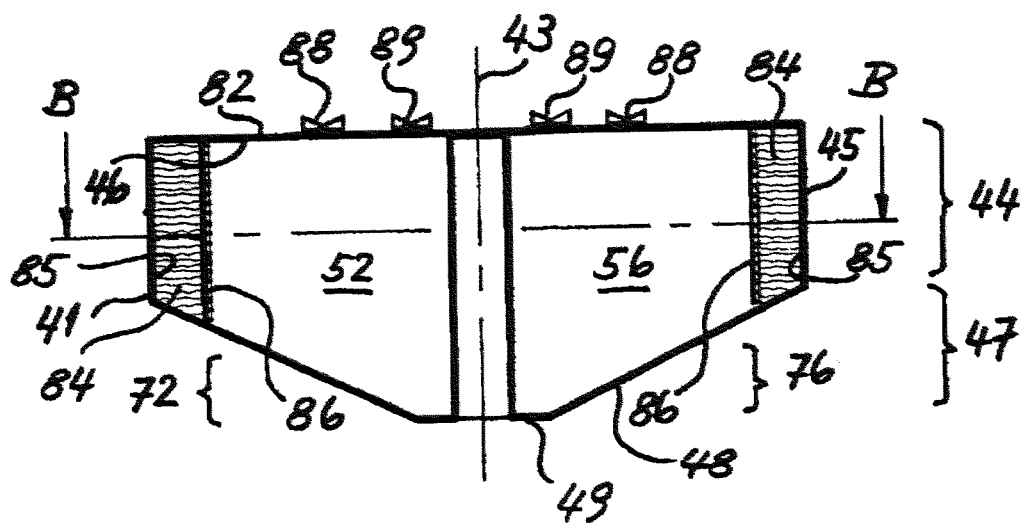
FIG. 11 shows a cross-sectional view of the device shown in FIG. 10 taken along a plane A-A.
Figure 12:
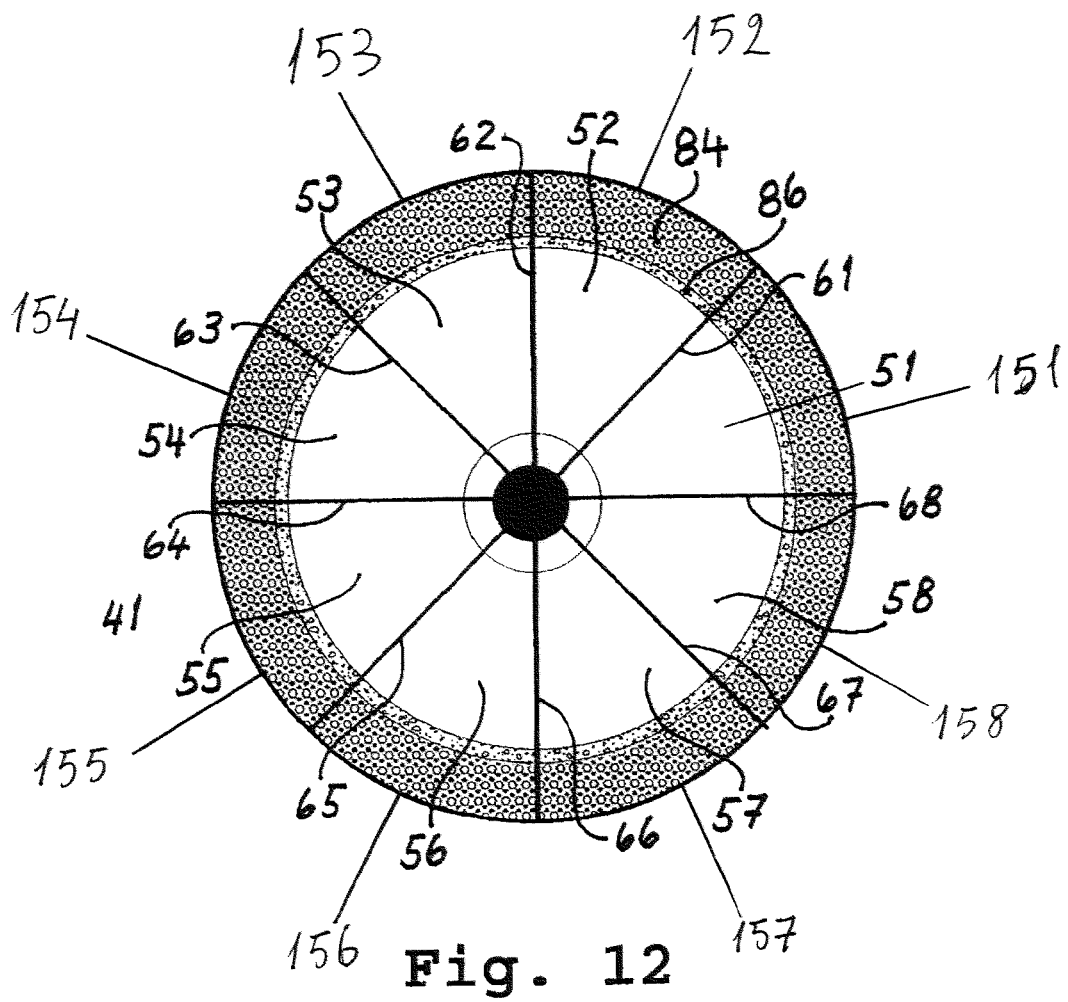
FIG. 12 shows a cross-sectional view of the device shown in FIG. 10 taken along a plane B-B in FIG. 11.

The device shown by FIGS. 10 to 12 further comprises a layer 84 of a retaining porous material which is arranged within each of the sections 151 to 158. The outer surface of layer 84 is in contact with and covers at least partially the inner surface 85 of the portion of the cylindrical side wall 45 which belongs to that compartment. In a preferred embodiment retaining porous material layer 84 covers the entire inner surface of the portion of the cylindrical side wall 45 which belongs to each section 151 to 158.

The device shown by FIGS. 10 to 12 further comprises a cover 82 of the upper opening 46 of container body 41. Cover 82 is fixed to container body 41. Cover 82 has at least one pipetting opening 89 for each of the sample compartments 51 to 58. The at least one pipetting opening 89 allows passage of pipetting needle therethrough for pipetting a blood sample into or out of one of the sample compartments 51-58. In a preferred embodiment cover 82 has a first pipetting opening 88 and a second pipetting opening 89 for each of the sample compartments 51 to 58. First pipetting opening 88 allows passage of a pipetting needle therethrough for pipetting a blood sample into one of the compartments 51-58. Second pipetting opening 89 allows passage of a pipetting needle therethrough for pipetting out of one of the compartments 51-58 a liquid component separated from that blood sample.

In a preferred embodiment, the device shown by FIGS. 10 to 12 comprises in addition a layer of separating permeable material 86 which is in contact with and extend at least partially over the inner surface of layer 84 of retaining porous material. In a preferred embodiment, layer 86 extends over the entire inner surface of layer 84.

Third Example of a Method According to the Invention

Figure 13:
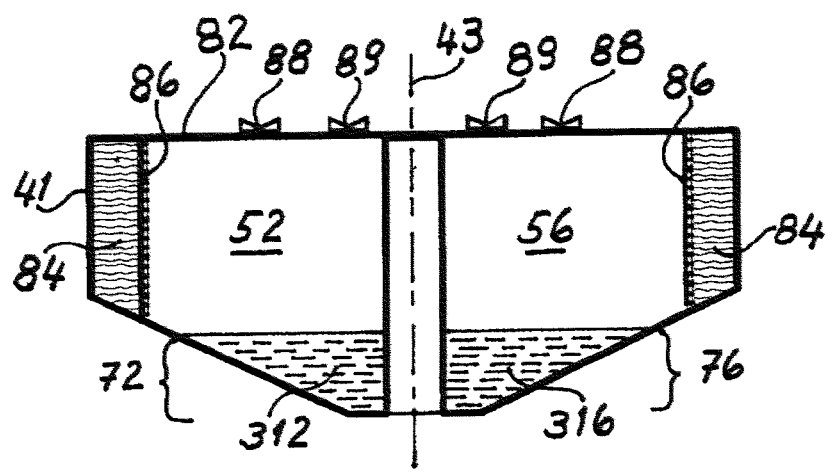
FIG. 13 shows a cross-sectional view of the device shown in FIG. 10 taken along a plane A-A and after blood samples have been loaded into compartments 52 and 56 of this device and with this device at rest.
Figure 14:
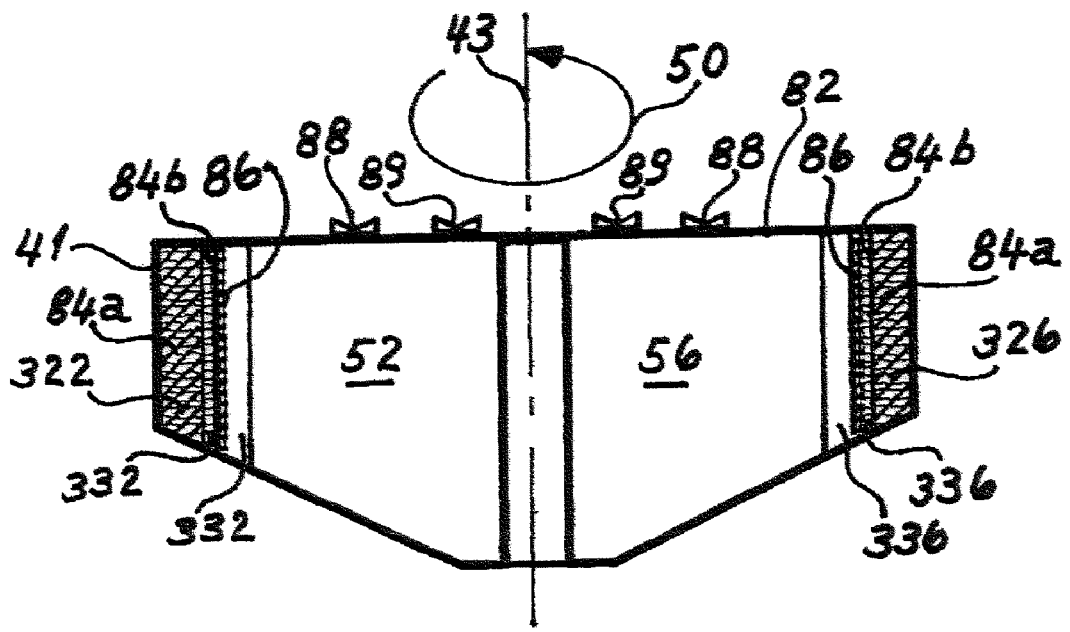
FIG. 14 shows a cross-sectional view of the device shown in FIG. 10 taken along a plane A-A and at the end of the axial centrifugation of container body 41, the centrifugation being effected by spinning the container body 41 about its symmetry axis 43.
Figure 15:
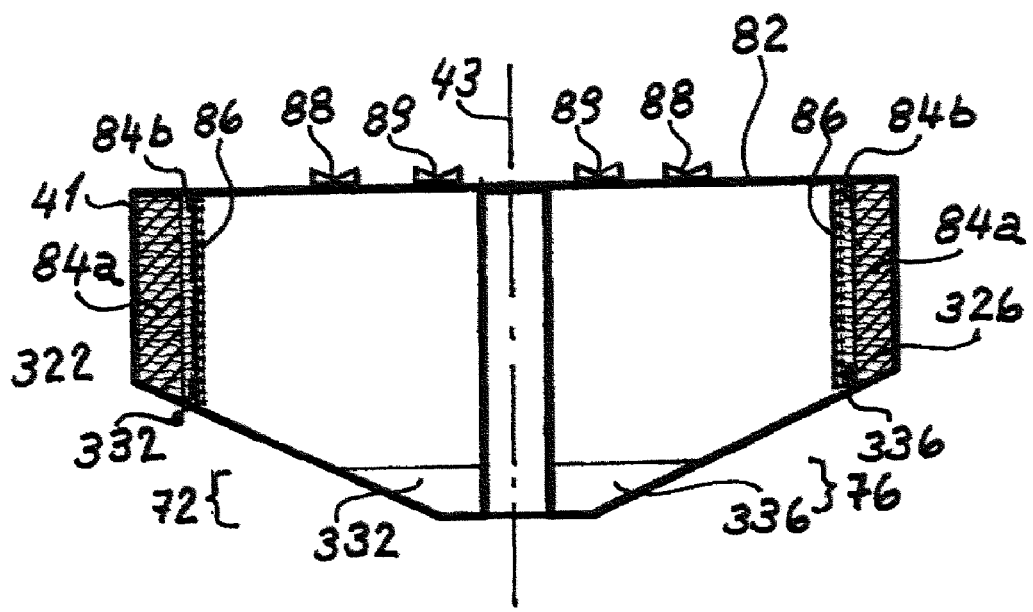
FIG. 15 shows a cross-sectional view of the device shown in FIG. 1 taken along a plane A-A after axial centrifugation of this device and with this device at rest.

A third example of a method according to the invention for separating a liquid component from a blood sample makes use of the device described above with reference to FIGS. 10 to 12 and comprises the following steps illustrated by FIGS. 13 to 15 which show compartments 52 and 56 of container body 41:

(a) introducing blood samples 312, 316 (shown in FIG. 13) into respective compartments 52, 56 of the container body 41 of a device according to the above described third example of a device according to the invention, (b) rotating the container body 41 about its symmetry axis 43 (as shown by FIG. 14) at a predetermined speed and in a sense shown by arrow 50 for separating the liquid components 332, 336 of the blood samples 312, 316 from the non-liquid components 322, 326 thereof, and (c) stopping the rotating of the container body 41, thereby allowing the liquid components 332, 336 of the blood samples 312, 316 to flow towards the central and bottom regions 72, 76 of the respective compartments 52, 56 of the container body 41, whereas the non-liquid components 322, 326 of the blood samples 312, 316 and portions of the liquid components 332, 336 of the blood samples 312, 316 are retained by layer 84 of the retaining porous material.

Step (b) is carried out with a rotation speed adjusted to a value in a range between 500 and 10000 rpm. The time required for the separation depends from the rotation speed. A decrease of the time required for the separation is obtained by increasing the rotation speed. In the case of centrifugation of the container body 41 the following are examples of rotation speeds used and of the values of the separation time achieved:

|  | Rotation speed | |
| --- | --- | --- |
|  | 500 rpm | 10000 rpm; |
| Separation time | 20 minutes | 15 seconds. |

With a rotation speed of 10000 rpm, separation of platelet-free plasma (<1000 platelets per µL) of a blood sample is achieved in a separation time lying in a range from 30 to 60 seconds.

After step (c) portions of the liquid components 332, 336 of the blood samples can be collected by means of a pipetting needle introduced through the pipetting openings 89 of cover 82 while the non-liquid components 322, 326 of the blood samples 312, 316 and portions of the liquid components 332, 336 of the blood samples 312, 316 are retained by layer 84 of the retaining porous material.

Layer 86 of separating permeable material is located between the sample compartment 52, 56 and the layer of retaining porous material 84. Non-liquid components of blood sample can pass through layer 86 of separating permeable material during centrifugation, while layer 86 of separating permeable material prevents the non-liquid components 32 from returning into the separated part of liquid component in the sample compartment 52, 56 after separation is completed.

The spatial distribution of the liquid component 332 and the non-liquid components 322 of blood sample 312 during centrifugation of container body 41 according to step (b) of the above described method and as schematically represented by FIG. 14 is similar to the spatial distribution shown by FIG. 5 where container body is a sample tube 11 with the only difference that the interior of container body 41 is subdivided in sections 151-158, whereas the interior of sample tube 11 is not. At the end of the centrifugation of container body 41 according to step (b), the non-liquid components 322, 326 of the blood sample in any of sample compartments 51-58 occupy a segment of an outer portion 84a of layer 84 of retaining porous material, whereas a first portion of the liquid components 332, 336 of the blood sample occupies an inner portion 84b of layer 84 of retaining porous material and a second portion of the liquid components occupy spaces each of which lies between layer 86 of separating permeable material and a space occupied by air 87 in the interior of a sample compartment 51-58 of container body 41.

In one embodiment of the above described method, each of the blood samples 312, 316 introduced into compartments 52, 56 of container body 41 by pipetting through pipetting openings 88 of cover 82 is obtained by means of a blood collection tube, the inside of which is under vacuum. This tube contains a coagulation preventing agent, and the blood sample 312, 316 is introduced into the blood collection tube by venipuncture. A coagulation preventing agent may be also or in alternative in sample compartments 52, 56 of container body 41. In this case the liquid components 332, 336 separated by the above described method are blood plasma.

In another embodiment of the above described method, each of the blood samples 312, 316 introduced into sample compartments 52, 56 of container body 41 by pipetting through pipetting openings 88 of cover 82 is obtained by means of a blood collection tube, the inside of which is under vacuum. This tube contains no coagulation preventing agent or contains a coagulation promoting agent, and the blood sample 312, 316 is introduced into the blood collection tube by venipuncture. A coagulation promoting agent may be also or in alternative in the sample compartments 51-58 of container body 41. In this case the liquid component 332, 336 separated by the above described method is blood serum.

After step (c) container body 41 and the separated liquid components 332, 336 contained in the compartments 52, 56 of container body 41 are usually kept at a suitable temperature until container body 41 and its contents are transferred to a clinical diagnostic analyzer apparatus for analysis of the liquid components 332, 336. However, the entire process may be executed by the same clinical diagnostic analyzer apparatus. The liquid components 332, 336 of the blood samples are aspirated then from the interior of a sample compartment 51-58 of container body 41 by means of a pipetting needle which is introduced into the compartments of container body through the pipetting openings 89 and aspirates samples of the liquid components 332, 336, and transfers them e.g. to reaction cuvettes of the clinical diagnostic analyzer apparatus.

In a preferred embodiment, step (b) is carried out with a centrifuge which is part of a clinical diagnostic analyzer which has an automatic pipetting unit and the blood samples to be processed are introduced by the latter pipetting unit through openings 88 of cover 82 of container body 41 into sample compartments 52, 56 of this container, and after the separation of the liquid and non-liquid components of the blood samples, the pipetting unit of the analyzer aspirates samples of the liquid components from the lower portions of sample compartments 52, 56 of container body 41, and this samples are analyzed in the clinical diagnostic analyzer.

In a preferred embodiment, in step (a) of the above described method a blood sample is loaded into each of the compartments 51-58 of container body 41.

Fourth Example of a Device According to the Invention

A fourth example of a device according to the invention is described hereinafter with reference to FIG. 16.

The structure of this device is similar to the structure of the device described above with reference to FIGS. 10 to 12, but in this fourth example each of the compartments 51-58 of container body 41 comprises in addition a photometric chamber 102, 106, which is fluidically connected with the interior of that compartment 52, 56 through an opening 92, 96 in the bottom wall 49 of the container body 41. Each of the photometric chambers 102, 106 is configured and dimensioned for enabling photometric measurement of a liquid contained therein. As shown by FIG. 16, photometric chambers 102, 106 have plane parallel side walls which extend downwards from opening 92, 96 in the bottom wall of the corresponding compartment 52, 56.

Figure 16:
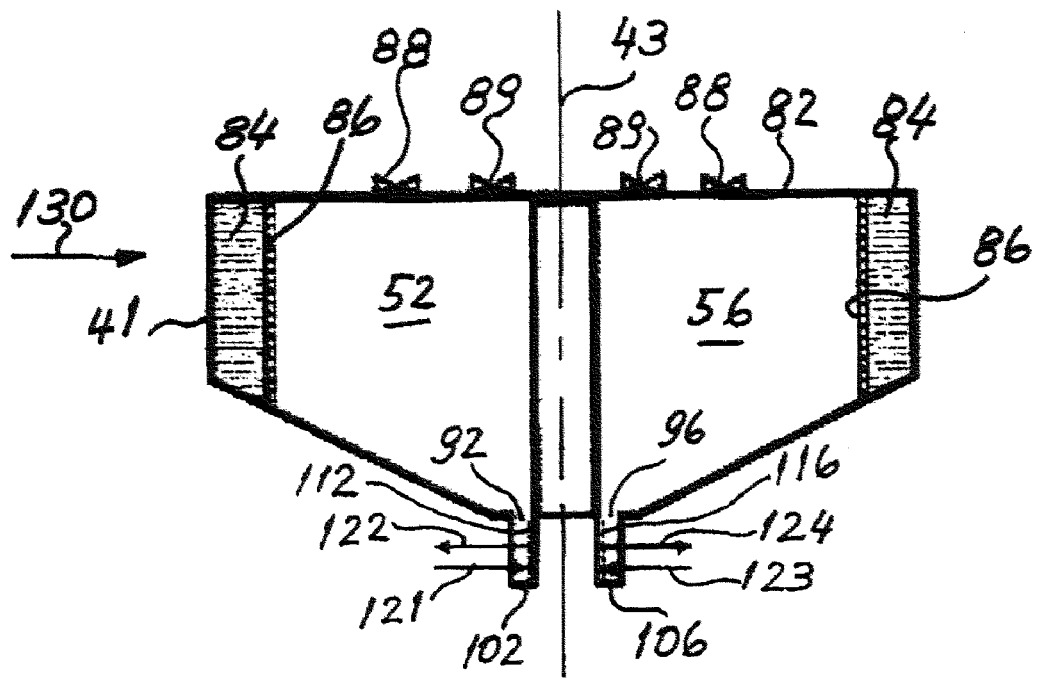
FIG. 16 shows a cross-sectional view of a variant of the device shown in FIG. 10.

FIG. 16 shows how mirrors 112, 116 can be integrated with the photometric chambers 102, 106, so that when an incident light beam 121, 123 is transmitted towards that chamber, a light beam 122, 124 is reflected by mirror 112, 116. The arrangement of a mirror 112, 116 in chambers 102, 106 enables a photometric measurement of a liquid contained in that chamber 102, 106.

Fifth Example of a Device According to the Invention

Figure 17:
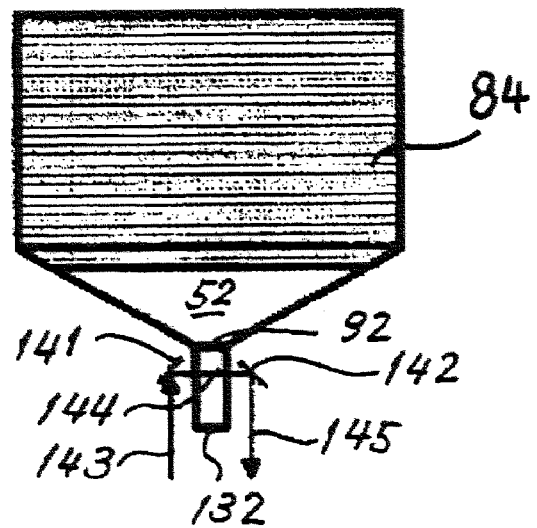
FIG. 17 shows a front view of a variant of the device shown in FIG. 16.

A fifth example of a device according to the invention is described hereinafter with reference to FIG. 17. This is a variant of the device shown in FIG. 16. FIG. 17 shows a front view seen from the direction indicated by arrow 130 of only one of the compartments of the device and shows a photometric chamber 132 which is fluidically connected with compartment 52 and which is suitable for performing photometric measurements.

As shown by FIG. 17, the chamber 132 of the device has plane parallel side walls which extend downwards from opening 92 in the bottom wall of the corresponding compartment 52.

FIG. 17, shows an example of how mirrors 141 and 142 may be arranged externally with respect to chamber 132 to guide light during photometric measurement of a liquid contained in that chamber. In this case an incident light beam 143 is transmitted towards mirror 141, a corresponding light beam 144 is reflected by mirror 141, passes through chamber 132, and is reflected by mirror 142 which emits a corresponding reflected light beam 145.

Fourth Example of a Method According to the Invention

A fourth example of a method according to the invention for separating a liquid component from a blood sample makes use of the device described above with reference to FIG. 16 or a device described above with reference to FIG. 17 and comprises the following steps:

(a) introducing blood samples 312, 316 (as shown in FIG. 13) into respective sample compartments 52, 56 of the container body 41 of a device according to the above described third example of a device according to the invention, (b) rotating the container body 41 about its symmetry axis 43 (as shown by FIG. 14) at a predetermined speed and in a sense shown by arrow 50 for separating the liquid components 332, 336 of the blood samples 312, 316 from the non-liquid components 322, 326 thereof, and (c) stopping the rotating of the container body 41, thereby allowing the liquid components 332, 336 of the blood samples 312, 316 to flow towards the central and bottom regions 72, 76 and into photometric chambers 102, 106, 132 of the respective sample compartments 52, 56 of the container body 41, whereas the non-liquid components 322, 326 of the blood samples 312, 316 and portions of the liquid components 332, 336 of the blood samples 312, 316 are retained by layer 84 of the retaining porous material.

Step (b) is carried out as in example three.

After step (c) a portion of the liquid components 332, 336 of the blood sample can be collected by pipetting through the pipetting openings 89 of cover 82 while the non-liquid components 322, 326 of the blood samples 312, 316 and portions of the liquid components 332, 336 of the blood samples 312, 316 are retained by layer 84 of the retaining porous material.

A layer 86 of separating permeable material is located between the sample compartment 52, 56 and the layer of retaining porous material 84. Non-liquid components of blood sample can pass through layer 86 of separating permeable material during centrifugation, while layer 86 of separating permeable material prevents the non-liquid components 32 from returning into the separated part of liquid component in the sample compartment 52, 56 after separation is completed.

In this fourth example of a method according to the invention a portion of the separated liquid component 332, 336 is collected in photometric chamber 102, 106 or 132 and therein photometrically determined.

Again, a coagulation preventing agent or a coagulation promoting agent may be used and plasma or serum respectively obtained.

In a preferred embodiment, in step (a) of the above described method a blood sample is loaded into each of the compartments 51-58 of container body 41.

Sample integrity checks including measurement of serum indices can be performed by photometric measurement of the serum sample contained in photometric chamber 102, 106 or 132.

The further processing of the contents of container body 41 after step (c) is e.g. as described above in the third example of a method according to the invention.

First Example of an Analytical Apparatus According to the Invention

A first example of an analytical apparatus according to the invention is e.g. a clinical diagnostic analyzer apparatus comprising a device as described above with reference to FIG. 1 and an arrangement for centrifuging the sample tube 11 of such a device about its symmetry axis 13.

In a preferred embodiment, this apparatus comprises a device as described above with reference to FIG. 6 and a detector comprising electro-optical means for performing photometric measurements of the contents of the photometric chamber 22 of that device.

Second Example of an Analytical Apparatus According to the Invention

A second example of an analytical apparatus according to the invention is e.g. a clinical diagnostic analyzer apparatus comprising a centrifuge to receive the device as described above with reference to FIGS. 10 to 12 and an arrangement for centrifuging the container body 41 of such a device about its symmetry axis 43.

In a preferred embodiment, this apparatus comprises a device as described above with reference to FIGS. 16 and 17 and electro-optical means for performing photometric measurements of the contents of the photometric chamber (cup) 102, 106 or 132 of that device.

Experimental Data

In a device of the type described above with reference to FIGS. 10 to 15, the container body 41 is made by injection molding of a suitable plastic material, has a diameter of 6.5 cm and comprises 8 compartments 51-58 having each a volume of 4.7 mL. In each compartment a layer of retaining porous material 84 and a layer of separating porous material 86 are arranged. The layer 84 has a volume of 0.95 mL and is foam S605oHY reticulated, by Koepp Schaum GmbH, Germany. Layer 86 is Nytex Nylon 03-171 by Sefar, Switzerland.

A volume of 1.5 mL of each blood sample from different patients contained in lithium heparin test tubes (Becton Dickinson Vacutainer®) are introduced in different compartments of container body 41.

The device is then rotated at 14000 rpm for 35 seconds with a centrifuge Minispin® Plus by Eppendorf, Germany.

After centrifugation, a volume of 500 mL plasma is collected from the lower portion of each compartment of container body 41.

The quality of these plasma samples is compared with the quality of reference plasma obtained from the same blood samples by a conventional method, centrifuging at 1900 g for 10 min with conventional centrifuge.

A measure of the quality of plasma is the measure of the number of platelets still present in the plasma. This was measured by an automated hematology analyzer KX-21N by Sysmex, Japan.

The average platelet number for the reference samples was about 25000 while the average platelet number for plasma obtained with the device of the present invention was about <1000.

It is thus clear that the device according to the present invention makes it possible to obtain plasma samples of high quality in a short time.

What is claimed is:

1. A separation device for separating at least part of the liquid component of at least one blood sample, said device comprising:
a container body being divided into a plurality of sections by partition walls; and
a plurality of sample compartments for receiving a plurality of said blood samples and retaining at least part of said separated liquid component after separation, wherein at least one of said sections comprises a layer of retaining porous material for retaining non-liquid components of said blood sample after separation,
wherein the at least one of said sections further comprises a layer of separating permeable material for preventing the non-liquid components of the blood sample from returning into the separated part of liquid component, and
wherein said separating permeable material is a mesh or stent comprising a large number of closely-spaced holes for the passage of matter with a size typical of non-liquid components of a blood sample under centrifugation conditions.

2. A separation device according to claim 1, wherein said separating permeable material is in contact with and extends at least partially over said layer of retaining porous material.

3. A separation device according to claim 1, wherein said layer of retaining porous material is chosen from a group comprising an open cell foam, a foamed rubber, a fleece, a mat, a honeycomb-like material or the like.

4. A separation device according to claim 1, wherein at least one of said compartments contains a coagulation preventing agent.

5. A separation device according to claim 1, wherein at least one of said compartments contains a coagulation promoting agent.

6. A separation device according to claim 1, further comprising at least one photometric chamber being fluidically connected with said at least one sample compartment through an opening in the bottom wall of the lower portion of said container body, said at least one chamber collecting at least a part of the separated liquid component and being configured and dimensioned for enabling a photometric measurement of said liquid component therein collected.

7. A separation device for separating at least part of the liquid component of at least one blood sample, said device comprising:
- a container body being divided into a plurality of sections by partition walls; and
- a plurality of sample compartments for receiving a plurality of said blood samples and retaining at least part of said separated liquid component after separation, wherein at least one of said sections comprises a layer of retaining porous material for retaining non-liquid components of said blood sample after separation,
- wherein the at least one of said sections further comprises a layer of separating permeable material for preventing the non-liquid components of the blood sample from returning into the separated part of liquid component,
- wherein said separating permeable material is a mesh or stent comprising a large number of closely-spaced holes for the passage of matter with a size typical of non-liquid components of a blood sample under centrifugation conditions, and
- wherein said mesh or stent is made of an inert polymer chosen from the group of Nylon, Teflon or the like.

* * * * *

UNITED STATES PATENT AND TRADEMARK OFFICE
CERTIFICATE OF CORRECTION

PATENT NO. : 8,040,505 B2  
APPLICATION NO. : 12/506323  
DATED : October 18, 2011  
INVENTOR(S) : Burkhardt et al.

Page 1 of 1

It is certified that error appears in the above-identified patent and that said Letters Patent is hereby corrected as shown below:

On the Title Page, Item (30) Foreign Application Priority Data "(EP) ............07001572" should read --(EP) ............07001572.2--.

Signed and Sealed this  
Fourteenth Day of February, 2012

David J. Kappos  
*Director of the United States Patent and Trademark Office*